US010278684B2

(12) United States Patent
Knight et al.

(10) Patent No.: US 10,278,684 B2
(45) Date of Patent: May 7, 2019

(54) SURGICAL APPARATUS COMPRISING MAGAZINE

(71) Applicant: Surgical Synergy Limited, Carmarthenshire (GB)

(72) Inventors: Martin Knight, Tenterton (GB); Roger John, Llanelli (GB)

(73) Assignee: Surgical Synergy Limited, Carmarthenshire (GB)

( * ) Notice: Subject to any disclaimer, the term of this patent is extended or adjusted under 35 U.S.C. 154(b) by 464 days.

(21) Appl. No.: 14/913,559

(22) PCT Filed: Aug. 22, 2014

(86) PCT No.: PCT/GB2014/052583
§ 371 (c)(1),
(2) Date: Feb. 22, 2016

(87) PCT Pub. No.: WO2015/025178
PCT Pub. Date: Feb. 26, 2015

(65) Prior Publication Data
US 2016/0213363 A1   Jul. 28, 2016

(30) Foreign Application Priority Data

Aug. 22, 2013 (GB) .................................. 1315030.5

(51) Int. Cl.
*A61B 17/00* (2006.01)
*A61B 17/29* (2006.01)
*A61B 90/98* (2016.01)

(52) U.S. Cl.
CPC ........ *A61B 17/00234* (2013.01); *A61B 17/29* (2013.01); *A61B 90/98* (2016.02);
(Continued)

(58) Field of Classification Search
None
See application file for complete search history.

(56) References Cited

U.S. PATENT DOCUMENTS 5,318,522 A * 6/1994 D'Antonio .......... A61M 5/2425
604/135
5,829,589 A 11/1998 Nguyen et al.
(Continued)

FOREIGN PATENT DOCUMENTS

DE   19537897 A1   3/1997
DE   10149421 A1   4/2003
(Continued)

OTHER PUBLICATIONS

International Search Report issued in co-pending foreign application No. PCT/GB2014/052583, dated Jan. 23, 2015.

*Primary Examiner* — Lynsey C Eiseman
(74) *Attorney, Agent, or Firm* — Dinsmore & Shohl LLP

(57) ABSTRACT

The present invention relates to a surgical apparatus including a magazine which is arranged to receive a plurality of medical interventions particularly for use in surgery. The surgical apparatus comprises a magazine including a plurality of chambers each adapted to store a medical intervention, the apparatus further comprising a probe adapted to interchangeably mate with the plurality of medical interventions wherein each chamber comprises an inlet access port to enable the probe to extend into the chamber and mate with a medical intervention therein and an outlet access port to enable passage of the probe including a medical intervention therefrom, the apparatus further comprising a first guide portion for guiding the probe to the magazine, a second guide portion aligned with the first guide portion for guiding the probe from the magazine and a positioning arrangement arranged to enable movement of the magazine relative to the first and second guide portions to enable selective alignment of the first and second guide portions with one of the plurality of chambers to enable passage of the probe therethrough.

14 Claims, 9 Drawing Sheets

(52) U.S. Cl.
CPC ........... *A61B 2017/00353* (2013.01); *A61B 2017/00362* (2013.01); *A61B 2017/00393* (2013.01); *A61B 2017/00473* (2013.01); *A61B 2017/00685* (2013.01); *A61B 2017/2903* (2013.01); *A61B 2017/2923* (2013.01); *A61B 2017/2926* (2013.01); *A61B 2017/2931* (2013.01); *A61B 2017/2933* (2013.01); *A61B 2017/2937* (2013.01)

(56) References Cited

U.S. PATENT DOCUMENTS

| | | | |
|---|---|---|---|
| 8,702,623 B2 * | 4/2014 | Parihar | A61B 10/0096 600/568 |
| 2003/0055409 A1 | 3/2003 | Brock | |
| 2008/0255413 A1 | 10/2008 | Zemlok et al. | |
| 2009/0005638 A1 | 1/2009 | Zwolinski | |
| 2011/0118756 A1 | 5/2011 | Brock | |

FOREIGN PATENT DOCUMENTS

| | | |
|---|---|---|
| DE | 102005058881 A1 | 6/2007 |
| DE | 102009025013 A1 | 12/2010 |
| WO | 9922650 A2 | 5/1999 |

* cited by examiner

SURGICAL APPARATUS COMPRISING MAGAZINE

The present invention relates to a surgical apparatus including a magazine which is arranged to receive a plurality of medical interventions particularly for use in surgery.

A considerable amount of time is spent during an operation in double-handing various instruments or medical interventions in particular during changing between instruments and the cleaning and removal of debris from the functional tip of the instruments. During endoscopic surgery, for example, a medical intervention such a tool is secured to a probe and the probe is subsequently inserted through a cannula. When the necessary work has been completed the probe is withdrawn from the cannula. The tool is manually removed from the probe, and is subsequently cleaned as necessary. The tip of the probe is also cleaned and a new instrument or medical intervention is attached to the probe for reuse.

A significant disadvantage associated with current practice is the time spent changing and cleaning the instrument and the tip of the instrument for securing to the tip of the probe. Furthermore, the surgeon and medical assistant must constantly be present in order that the surgeon has the correct instrument attached to the probe. As the surgeon turns the probe to the point of procedure the medical assistant completes cleaning of the probe that has been removed and also prepares a subsequent probe ready for use.

Aspects of the present invention provide significant advantages.

According to a first aspect of the present invention there is a surgical apparatus comprising a magazine including a plurality of chambers each adapted to store a medical intervention, the apparatus further comprising a probe adapted to interchangeably mate with the plurality of medical interventions wherein each chamber comprises an inlet access port to enable the probe to extend into the chamber and mate with a medical intervention therein and an outlet access port to enable passage of the probe including a medical intervention therefrom, the apparatus further comprising a first guide portion for guiding the probe to the magazine, a second guide portion aligned with the first guide portion for guiding the probe from the magazine and a positioning arrangement arranged to enable movement of the magazine relative to the first and second guide portions to enable selective alignment of the first and second guide portions with one of the plurality of chambers to enable passage of the probe therethrough.

The first aspect of the present invention provides significant benefits in that a probe can be aligned with and subsequently secured to a medical intervention (including medicine, drugs, a medical instrument or a tool) with the intervention retained in the magazine and then taken to the point of procedure by the probe. There is no time wasted in searching for the correct interventions as they are retained in the magazine. The magazine can be prepared prior to surgery. As such speed of changeover is increased. Once the part of the procedure requiring that intervention has been completed the probe can be withdrawn into the magazine, the intervention removed and the movement of the magazine enables realignment of the probe with an alternative chamber for connection to a different medical intervention. In this manner a different medical intervention can quickly be selected for use by the surgeon without withdrawal of the probe (and used medical intervention) from the apparatus. The used medical intervention, particularly in the case of a tool, can then be removed from the magazine as appropriate for cleaning or may be retained within the magazine for cleaning following completion of the surgical procedure. Furthermore, the medical intervention can be positioned in a pre-defined order within the magazine meaning that the correct medical interventions for a procedure are preselected and stored in the magazine ready for completion of the operation.

The positioning arrangement is beneficially adapted to enable the magazine to rotate relative to the first and second guide portions. The positioning arrangement preferably includes a frame. The frame preferably retains the magazine at retaining points spaced apart in the longitudinal axis of the magazine. The longitudinal axis is the axis about which the magazine rotates. The retaining points are preferably at opposing ends of the magazine.

The first and second guide portions beneficially include a tubular element through which the probe can pass. The first guide portion guides a probe from a first location outside the magazine through the inlet access port into a chamber in the magazine. At this location the probe mates with an intervention to give positive engagement between probe and intervention. The second guide portion enables receipt of the probe including a medical intervention connected thereto from the magazine for passageway into a body, and may comprise in part or in whole a cannula. The inlet of the second guide portion and outlet of the first guide portion are beneficially aligned. A substantially linear pathway is therefore beneficially defined between the first guide portion and second guide portion and a chamber of the magazine. The second guide portion is beneficially elongate. The second guide enables the medical intervention mated to the probe to be transported to the medical site.

It is beneficial that the positioning arrangement is adapted to enable the magazine to rotate relative to the first and second guide portions. It will be appreciated that linear movement of the magazine relative to the guide is also possible as shown in the exemplary embodiments. A frame is beneficially provided having first and second magazine engagement elements spaced apart in a longitudinal axis. The magazine can thus rotate relative to the frame. A motor may be provided for causing movement of the magazine relative to the first and second guide portions. It will be appreciated that the apparatus may be automated such that a surgeon can identify via a user input when a particular medical intervention is required and a signal may cause the motor to transfer between medical interventions without requiring manual intervention.

A medical intervention is beneficially provided in a plurality of the plurality of chambers. Medical intervention may take a variety of forms and may include medicine, drugs, a medical instrument or a surgical tool for example.

The medical interventions beneficially include an identifier provided in co-operation with the medical intervention. For example, the identifier may be radio frequency tag which is adhered or otherwise secured to the medical intervention. This ensures that the location of the medical intervention is always known and therefore the medical intervention cannot be accidentally left within the patient. Traceability of the medical intervention is thus ensured. The inlet access port and outlet access port of each of the chambers are beneficially aligned in the longitudinal axis. This means that the probe mates with a selected medical intervention through the inlet access port and into the chamber and out of the outlet access port with ease.

The inlet access port and outlet access port of the plurality of chambers are preferably sealed. The medical intervention is therefore in sterilized form prior to use. The seal forms a membrane which is burst or parted upon communication with the probe or medical intervention dependent upon whether the seal is on the inlet access port or the outlet access port. A further seal is beneficially provided in the second guide portion. This may be parted by the intervention and is beneficial for example to retain gas or fluid in a body in order to perform a procedure.

The magazine preferably includes a plurality of modules configured to be removable from the magazine, wherein each module includes one or more chambers therein. The module is effectively a cartridge and each module preferably includes one chamber. It is beneficial that the module is laterally removable from the magazine. The module is therefore preferably removable in an axis substantially perpendicular to the longitudinal axis of the magazine and perpendicular to the longitudinal axis defined between the inlet access port and outlet access port. A significant benefit is associated with this aspect of the invention.

In the event that a surgical procedure requires a different tool for example such a tool can be readily inserted into the magazine via a new module whilst operation upon a patient continues. Furthermore, a biopsy for example may be collected from a patient and withdrawn into the magazine and immediately removed for analysis whilst the surgeon carries on with the surgical operation. This saves a significant amount of time in what can be extremely long surgical operations. Furthermore, there is no handling of the biopsy other than handling of the module.

The magazine preferably includes a plurality of slots where each slot is adapted for receipt of a module. The slot engages with the module where opposing jaws defining the edge of the slot secure the module within the slot. The slot is preferably elongate and extends in the longitudinal axis. The slots are preferably spaced apart and extend around a majority of the peripheral edge of the magazine. The slots are preferably positioned parallel to one another and are preferably aligned in a transverse axis.

Each of the slots and modules are beneficially adapted to mate in only one orientation. This is beneficial as this ensures that a module cannot be loaded into the cassette in the incorrect orientation.

The modules beneficially include an identifier for identifying the medical intervention therein. The identifier may be identification wording or may simply be a colour associated with the body of the module which identifies to the surgeon the medical intervention therein.

The second guide portion preferably comprises a proximal end in connection with an outlet access port of a chamber and a distal end having an opening for enabling a medical intervention to pass therethrough, the second guide portion including at least one access port. The at least one access port is beneficially closer to the proximal end of the second guide portion than the distal end of the second guide portion. Beneficially, the at least one access port it positioned adjacent to the proximal end. This enables communication with a suction arrangement for example to remove debris from the surgical site or a gas inlet for example.

According to a further aspect of the present invention there is a magazine comprising at least a first and second chamber adapted to each store a medical intervention, each of the first and second chambers comprising an inlet access port and an outlet access port.

The first inlet access port and first outlet access port are beneficially aligned in a longitudinal axis of the magazine.

The magazine preferably includes a plurality of modules configured to be removable from the magazine, wherein each module preferably includes the chamber therein.

The module is preferably laterally removable from the magazine.

The magazine preferably includes a plurality of slots for receipt of the module.

Each of the slots and modules are preferably adapted to mate in only one orientation. The modules preferably include an identifier from identifying the medical intervention therein.

The first and second chambers are configured to house a medical intervention and are preferably sealed. A sealing means if preferably provided. This has the benefit that the intervention can be sterilised. A non-reusable seal is therefore preferably provided to seal the inlet access ports and outlet access ports.

There is beneficially provided motive means for causing movement of the magazine. More preferably the motive means moves the magazine relative to the first and second guide portions. Preferably the motive means is an electric motor. There is further preferably a control means for causing actuation of the motive means to align the inlet access port of the magazine with the guide. The plurality of chambers are preferably spaced around a central axis of rotation of the magazine. The magazine is preferably substantially cylindrical and the modules may form segments of the magazine.

The positioning arrangement preferably includes a frame for receipt of the magazine. Another aspect of the present invention relates to the remote operation of a surgical tool. According to a further aspect of the present invention there is an apparatus for remote operation of a surgical tool comprising:

a drive element arranged to communicate with a tool head;
a tool head including a tool actuator and a tool element;
wherein the tool actuator is configured to translate rotational movement of the drive element to linear movement of the tool element.

This enables a surgeon to operate a tool element such as a grasper or scissors for example remotely but with dexterity and control.

The drive element is beneficially releasably communicable with the tool head.

The drive element is beneficially in communication with a user operable input arrangement. The drive element beneficially links the user operable input arrangement to the tool head. The user operable input arrangement is beneficially remote to the distal end of the drive element, where the distal end of the drive element communicates with the tool head. In use the user operable input arrangement is operable outside of the patient whilst the drive element extends through a cannula internally of a patient.

The user operable input arrangement is beneficially secured to the drive element at the proximal end thereof. The user operable input arrangement is beneficially arranged to cause rotation of the drive element. The user operable input arrangement beneficially comprises an arrangement to convert linear input force to rotational force of the drive element. Such an arrangement may be, for example, a rack and pinion mechanism. A surgeon actuates the user operable input arrangement preferably via squeezing a trigger providing control to the rotation of the drive element. The input linear force is converted to a rotational force effecting rotation of the drive element. A maximum rotation of the drive element is restricted by the distance of depression of the trigger.

Beneficially the drive element rotates rather than moves linearly. This enables better control and accuracy of control of rotation meaning the speed of movement of the tool element is better controlled.

The drive element may be flexible. The drive element may be a cable. This enables non-linear access into a patient, through for example a non-linear cannula.

The tool head is preferably provided as a module. This means that the tool head may be provided as a standalone device. This means different surgical tools may be selected quickly for use without requiring complex changeover procedure. The tool heads are beneficially provided in a magazine and may be located in a predetermined order within the magazine for use according to a particular surgical procedure. Aspects of the apparatus for storing a medical intervention (such as a surgical tool) including the magazine are described elsewhere in the specification and can be utilised with and are beneficial with the use of the apparatus for remote operation of a surgical tool.

The tool head beneficially includes a tool actuator configured to translate rotational movement of the drive element to linear movement of the tool element where the tool element could be a grasper, cutter, finger, scissors or other tools which will clearly be appreciated by the skilled addressee.

The tool actuator is beneficially arranged to enable movement of the tool element. In the case of a grasper, for example, the tool actuator converts rotation of the drive element to enable opening and closing of the jaws of the grasper.

The tool actuator preferably comprises a driver which beneficially comprises a socket arranged to receive the distal end of the drive element. It is beneficial that the tool actuator and drive element cooperate in order to transfer rotational movement of the drive element to the tool actuator. In one embodiment a socket is preferably shaped to receive a shaped distal end of the drive element to match the profile of the socket, so, for example, the drive element may be of a square profile received in a correspondingly shaped square profiled socket. Other profiles are envisaged and the opposite configuration could potentially be utilised wherein the drive element includes a socket at a distal end thereof arranged to receive a portion of the tool actuator. Furthermore, other profiles are envisaged such as a splined configuration.

The tool actuator and preferably the driver further comprise a helix utilising an Archimedes screw principle. The tool actuator preferably further comprises a tool element contact portion. The helix of the tool actuator seats into a corresponding helix in a tool element contact portion. In use the tool actuator helix rotates but remains in a constant axial position causing the non-rotating tool element contact portion which cannot rotate to be drawn axially meaning that rotation of the drive element causes linear movement of the tool element contact portion.

The tool element contact portion preferably comprises a plurality of fingers and means to locate about the tool element. The fingers preferably sit on top of the jaws of the tool element. The jaws preferably include a biasing means to bias the jaws to a closed configuration. Movement axially of the tool element contact portion preferably causes pulling apart of the jaws against the biasing means. The opposite configuration where the jaws are biased open is possible, however, for safety purposes it is beneficial to bias the jaws to a closed configuration.

The tool head preferably further includes a tool body. The tool body is preferably configured to at least partially accommodate therein the tool element contact portion. Preferably the tool body is configured to accommodate the tool element, and preferably is arranged to receive the jaws of the tool element to enable the jaws to pivot relative to the tool body. The tool body preferably also houses the tool actuator.

The apparatus preferably further includes an elongate housing which may be termed a probe arranged to at least partially house the drive element. The elongate housing preferably has a first end arranged to communicate with the user operable input arrangement. The elongate housing preferably has a second end arranged to engage with the tool body. The elongate housing is beneficially arranged to secure to the tool head and in particular preferably the tool body. In this way the elongate housing, including the drive element therein, can be brought into contact with the tool head. Once engaged the tool can be actuated. A collar is preferably provided moveable axially between and unsecured and a secured configuration wherein the secured configuration the collar ensures engagement (thereby preventing unintentional release) of the elongate housing with the tool head.

The elongate housing preferably has a male engaging portion. The tool head and even more preferably the tool body preferably defines a female engaging portion. The collar is preferably arranged to be moveable over the tool body. The tool body beneficially includes a plurality of fingers arranged to be compressed by the collar. The collar preferably is slidable along a helix and movement of the collar may be actuated by a user input means, for example a lever, beneficially provided on the magazine.

Aspects of the present invention will now be described by way of example only with reference to the accompanying drawings in which:

FIG. 9 shows the individual components separate and FIG. 9 shows the individual components assembled of the elongate housing and tool head according to exemplary embodiments of aspects of the present invention.

Figure 1A:
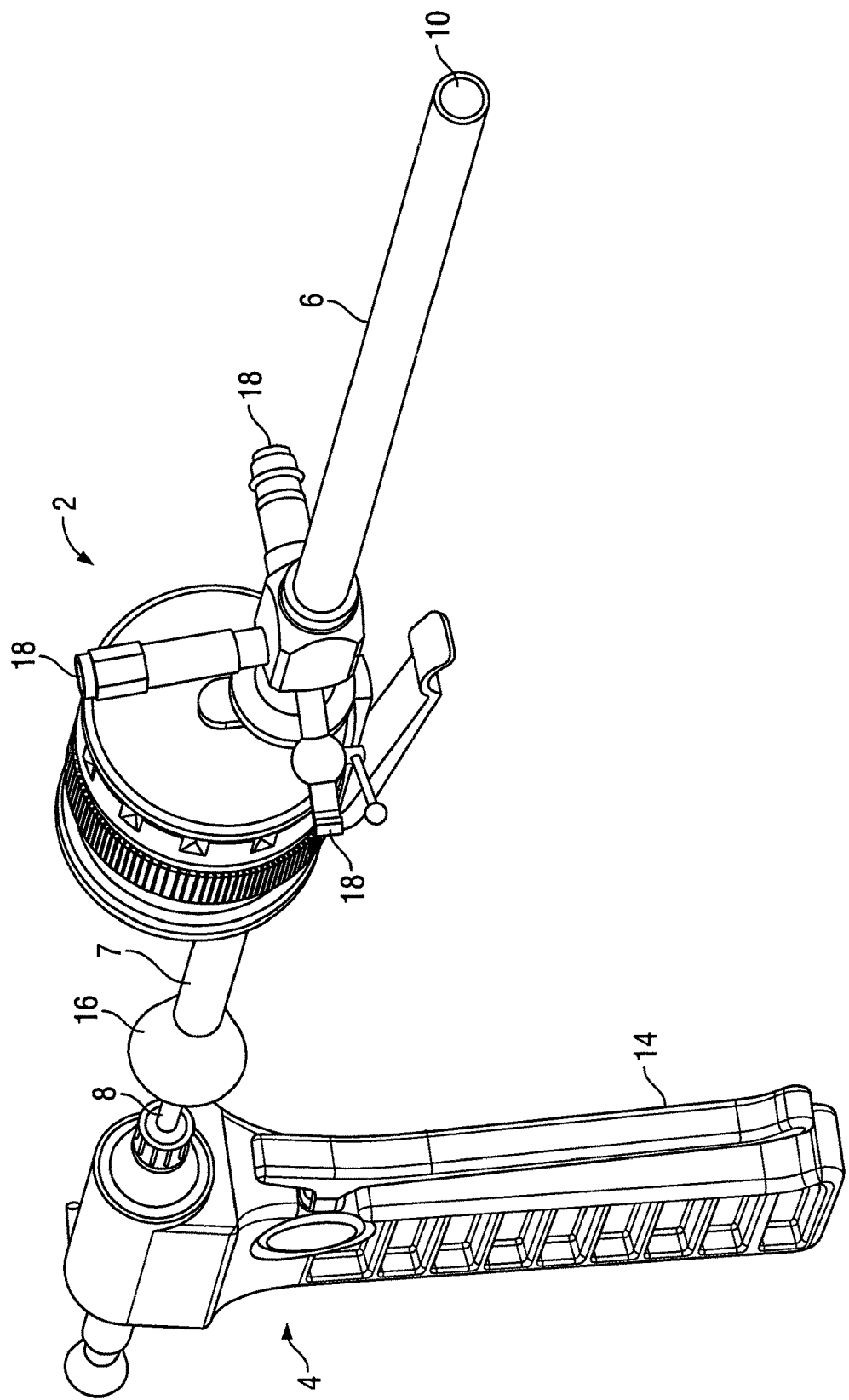
FIGS. 1a and 1b are schematic perspective views including exemplary embodiments of the present invention.
Figure 1B:
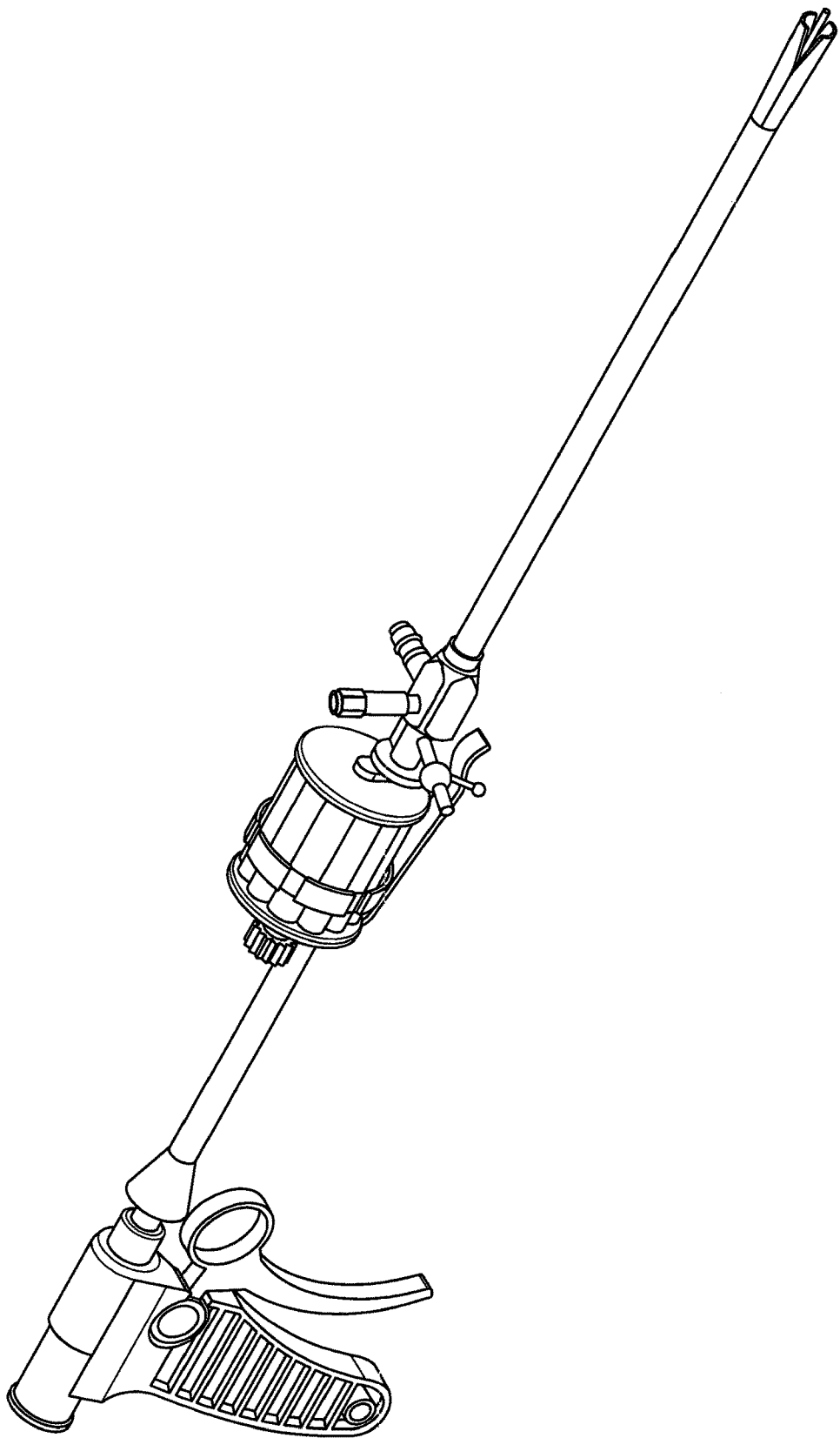
Figure 3:
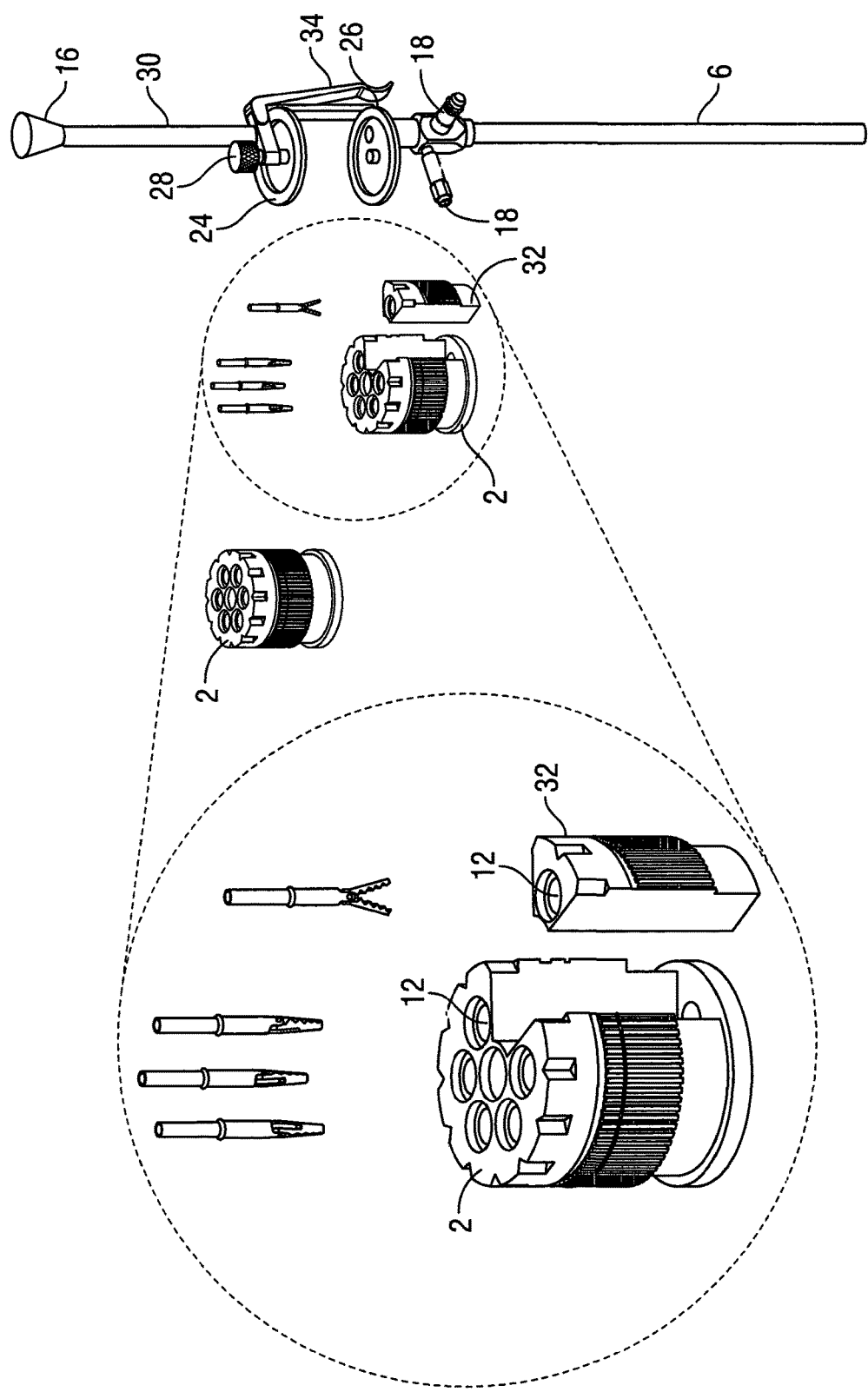
FIG. 3 is a schematic perspective view showing the magazine in more detail according to an exemplary embodiment of aspects of the present invention.

Referring to FIGS. 1a and 1b, schematic perspective views of apparatus embodying aspects of the present invention are shown presenting alternative magazines configurations which will be described in more details later. There is provided a magazine (2) arranged to rotate in a longitudinal axis to selectively align a chamber (3) as shown in FIG. 3 provided therein with a second guide portion which is generally termed a cannula (6). The chambers (12) are each arranged to house a medical intervention which may include drugs, medicines, medical instruments or tools for example. A user operable input arrangement is beneficially provided for operation by a user who is performing the operation on the patient which includes an elongate element (8) which may be termed a probe (8) having at a distal end a tool (9) (but not shown in FIG. 1) which is inserted through a first guide portion (7), and into the chamber (6) of the magazine (2) where the distal end mates with a tool (9). The probe (8) and tool (9) is then transferred through the second guide portion or cannula (6) into the patient. The user operable input arrangement includes a trigger (14), operation of which controls actuation of the tool (9) provided at the point of procedure (10). One or more supplementary inlets (18) are beneficially provided to provide suction, irrigation or gases to the working end of the apparatus or point of procedure (10).

Figure 2:
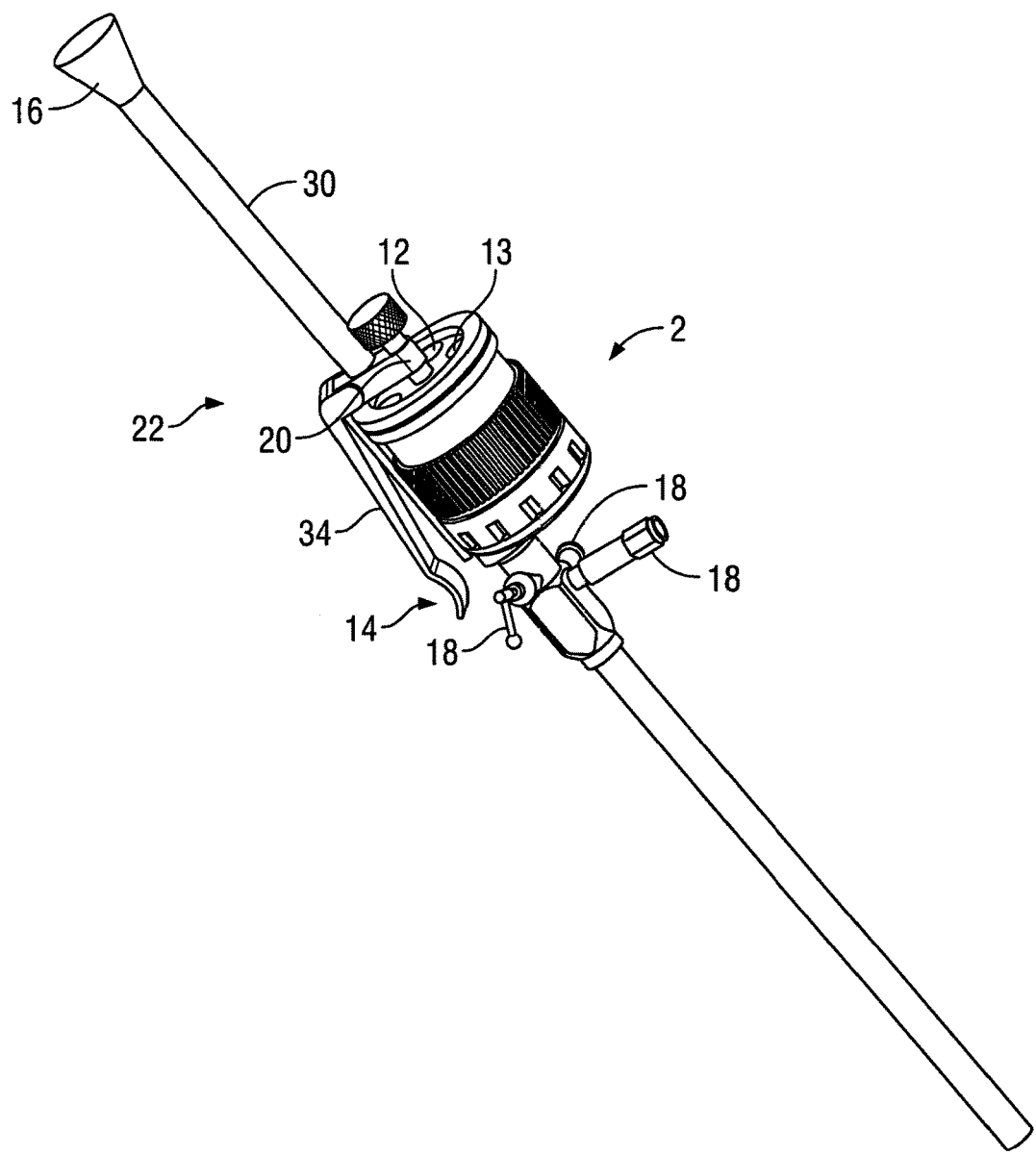
FIG. 2 is a schematic perspective view of a magazine according to exemplary embodiments of aspects of the present invention.

Referring now to FIG. 2, the magazine (2) is shown in more detail without the user operable input arrangement (4). The magazine (2) comprises a plurality of chambers (12), each of which are arranged to receive a medical intervention. Each of the chambers (12) include an inlet access port (13) and an outlet access port (not shown) where the outlet access port is aligned with the cannula (6). The chambers (12) are spaced apart radially around an axis of rotation (20). Each of the chambers (12) are preferably sealed meaning that the medical intervention is sealed within the chamber (12). This may be achieved via a breakable seal which is burst by contact with the probe (8) or tool (9) which covers the inlet access port (13) and outlet access port.

The magazine (2) is held by a positioning arrangement which is configured to selectively align a probe with a selected chamber (12). A control arrangement may be provided to enable selective alignment between chambers, or there may be a predetermined or pre-programmed sequence. The positioning arrangement is generally indicated by reference numeral (22) and may include a frame (24) for accommodating the magazine (2). This is shown more clearly in FIG. 3 whereby the frame (24) comprises a projection or engagement element (26) for accommodating a first end of the magazine (2) and an adjustable element (28) moveable relative to the frame (24) to enable securing of the magazine (2) within the frame (24). The projection (26) may rotate as a whole with the magazine in relation to the rest of the frame (24) or may be fixed in position and the magazine rotate around the retaining lug (27). As such, the magazine (2) as a whole may be removed and replaced as appropriate. The frame (24) enables rotation of the magazine (2) relative to the frame but is arranged to ensure that a chamber (12) aligns with the cannula (6) and also a first guide portion (7) of the positioning arrangement (22). The first guide portion (7) includes an inlet (16) which is tapered outwardly to receive a distal end of the probe (8). Utilising a positioning arrangement in the exemplary embodiment where the magazine (2) is arranged to rotate is functionally beneficial for compactness of the apparatus, however, it will be appreciated that the positioning arrangement (22) may be arranged to enable linear rather than rotational movement of a magazine (2) if the chambers are linearly aligned.

An actuator (34) is beneficially provided which will be described in more detail later in the specification. The purpose of the actuator (34) is to prime the distal end of the elongate housing (8) to enable engagement with the tool head.

With reference to FIG. 3, it will be appreciated that each of the chambers may be provided within a module (32) which may be withdrawn from the magazine (2) for cleaning, transfer of tissue (such as biopsies), replacement with a different intervention etc. This is described in more detail with respect to FIGS. 5-7.

Figure 4:
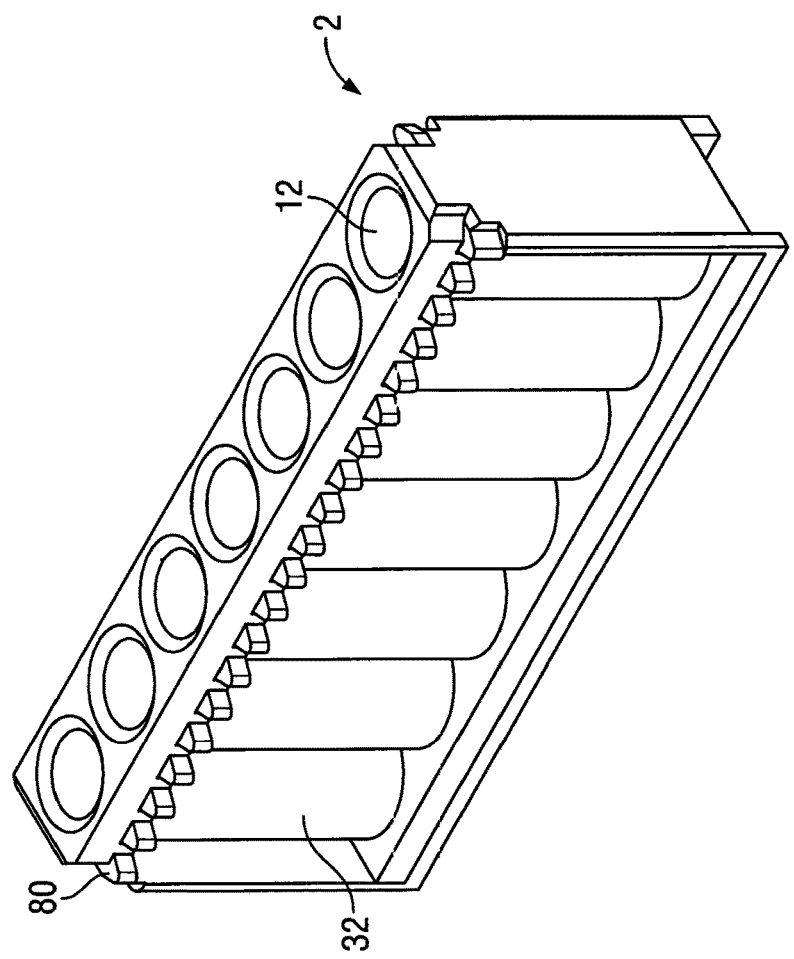
FIG. 4 is a schematic perspective view of a magazine according to an exemplary embodiment of the present invention.

Referring to FIG. 4, a magazine (2) is schematically presented having plurality of chambers (12) where the magazine (2) is arranged to move linearly with respect to the positioning arrangement. As such the chambers (12) are positioned in a side-by-side configuration. A plurality of teeth (80) are provided to enable co-operation with corresponding teeth enabling movement of the magazine to relative to the positioning arrangement. It will be appreciated that in the schematic diagram presented modules (32) are not removable however it will be appreciated that this is a desirable design configuration.

Figure 5:
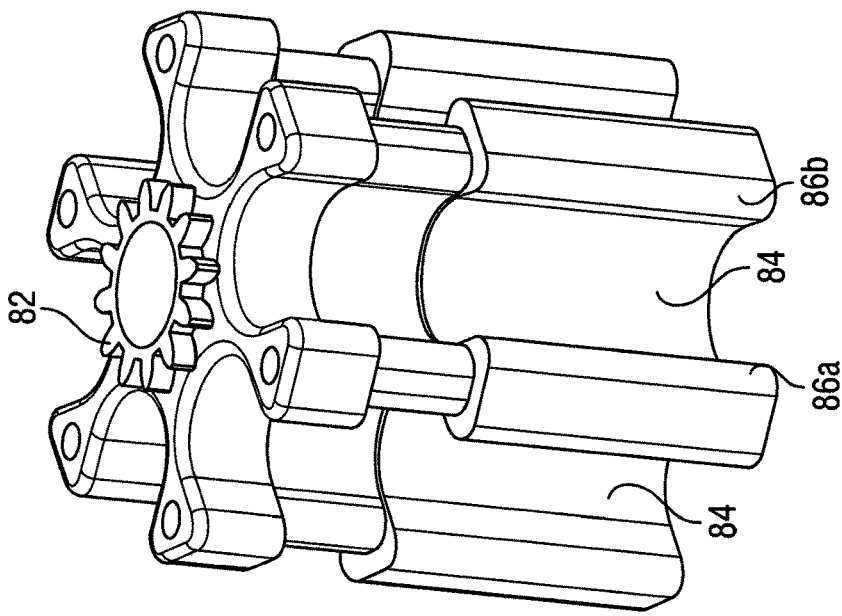
FIG. 5 is a schematic perspective view of a magazine without modules incorporated therein according to an exemplary embodiment of the present invention.

Referring now to FIG. 5 there is a schematic perspective view of a magazine according to an exemplary embodiment of the present invention. The magazine has a longitudinal length and at a first end comprises a co-operating element (82) in the form of a cog that co-operates with the positioning arrangement to enable rotation of the magazine. A plurality of elongate slots (84) are provided which are outwardly open. The slots are defined between opposing jaws (86a, 86b) where the jaws (86a, 86b) are discontinuous along the longitudinal length to receive a corresponding portion of a module. This is important to ensure that incorrect locating of a module into the magazine is prevented. The modules are clipped into the slot (84) in a direction substantially perpendicular to the longitudinal length of the magazine. Furthermore, such a configuration prevents incorrect positioning in the longitudinal axis of the module and prevents sliding in the longitudinal axis. It will be appreciated that the benefit of providing modules and in particular modules that can be withdrawn laterally is that on the fly changing of the modules can occur for example to remove biopsies or due to a sudden change in the operation procedure whereby for example a different tool is required.

Figure 6:
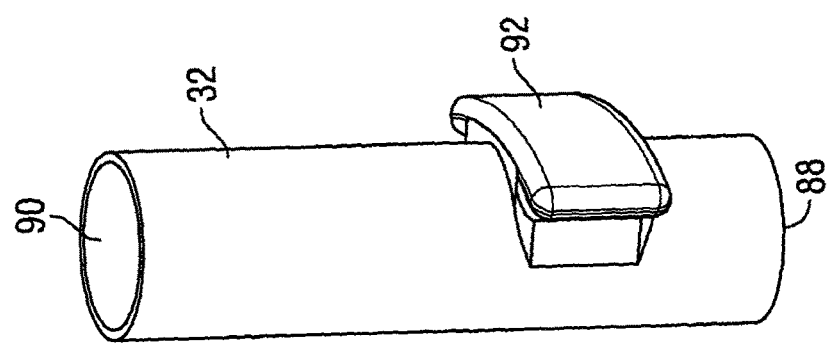
FIG. 6 is a schematic perspective view of a module arranged to contain a medical intervention therein for mating with a cassette as presented in FIG. 5 according to an exemplary embodiment of the present invention.

Referring now to FIG. 6 there is a module (32) containing therein a medical intervention. A seal is provided at the inlet access port (88) and the outlet access port (90). The protrusion (92) is configured to be received in the interruption in the jaws (86a, 86b) of the slot (84).

Figure 7:
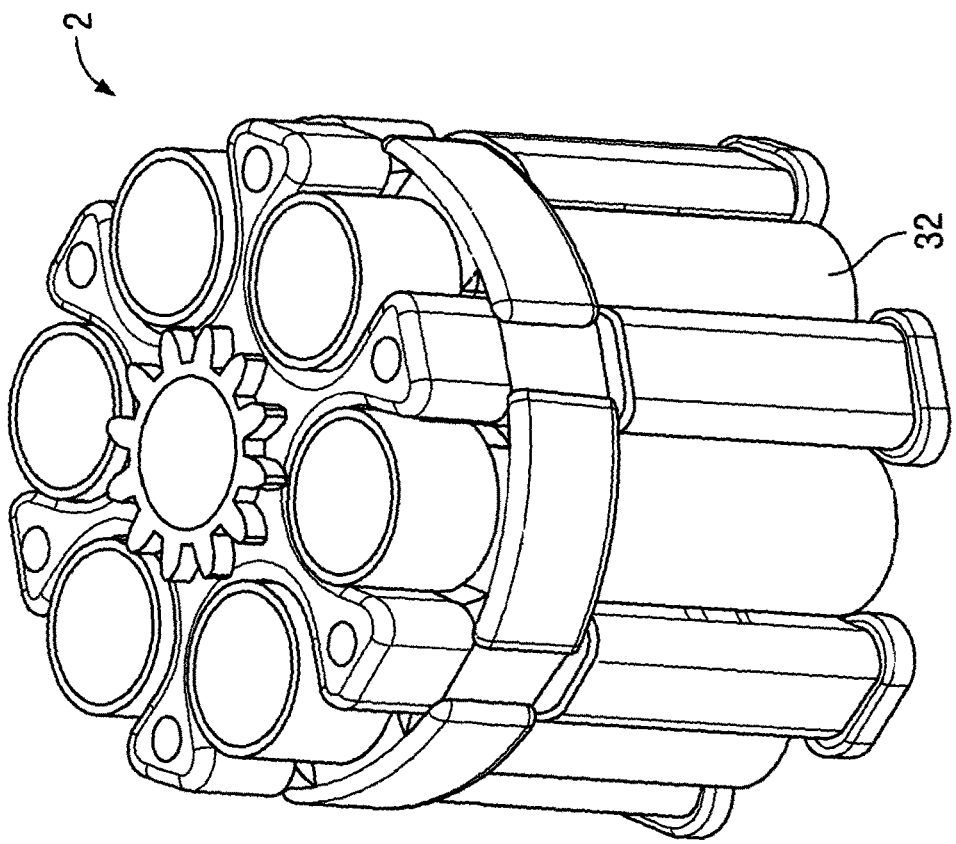
FIG. 7 is a schematic perspective view of a magazine according to an exemplary embodiment of the present invention including the module as presented in FIG. 6.

Referring now to FIG. 7 an exemplary embodiment of the magazine is presented with six modules each containing medical interventions therein located into the magazine body. Such a magazine is then ready for use.

Figure 8:
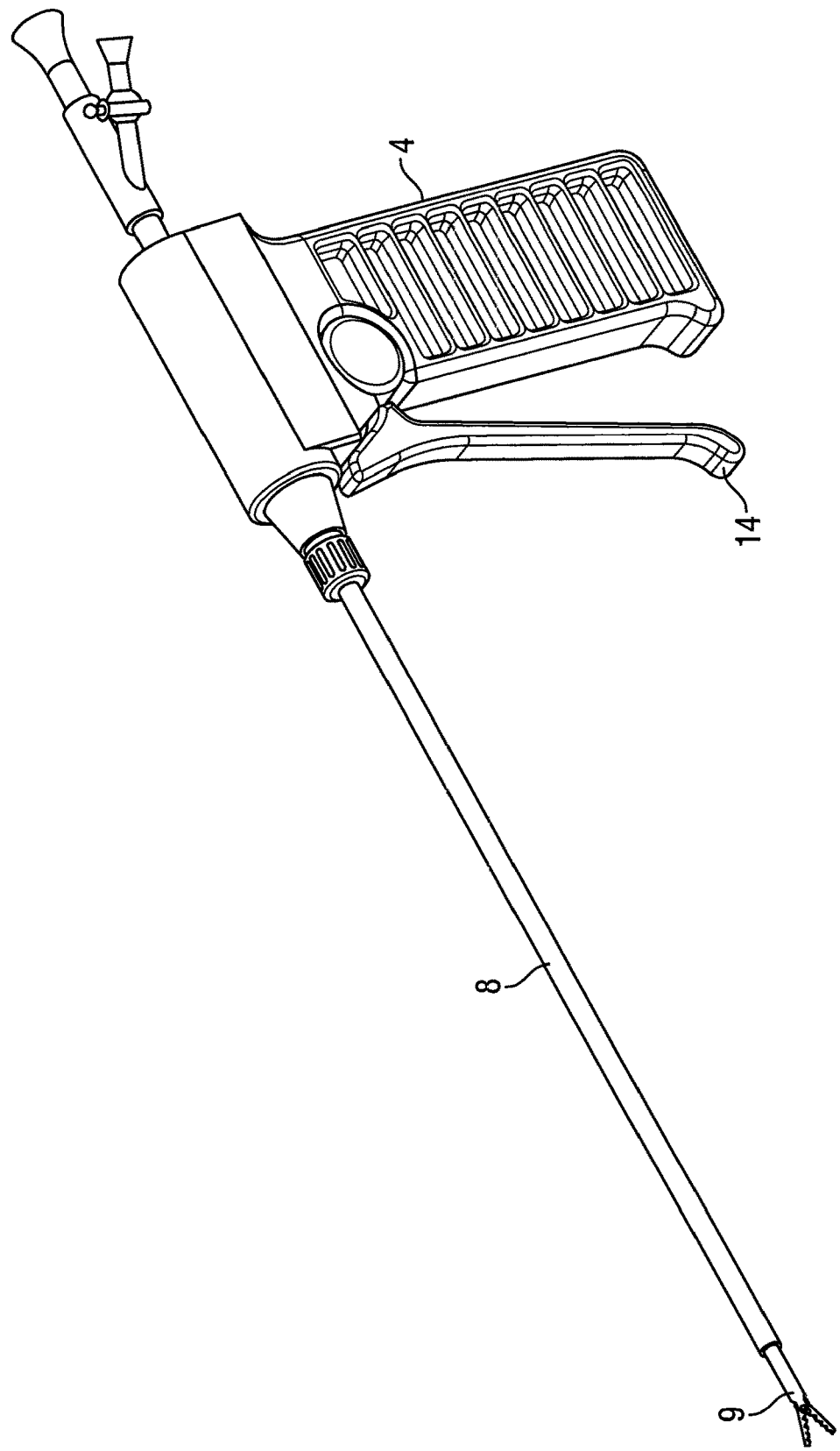
FIG. 8 is a schematic perspective view of a user operable input arrangement, elongate housing and tool head according to an exemplary embodiment of aspects of the present invention.

Referring now to FIG. 8, there is a schematic perspective view of the user operable input arrangement (4) without the magazine and positioning arrangement used to control movement of the tool (9) that has been mated to the probe (8). The probe (8) itself may be a housing as described therein. Once a tool (9) has been received onto the probe (8) then the tool and probe (8) extends through the magazine down the cannula (6) to the point of procedure (10). Control of the tool (9) is provided by compression and release of the trigger (14).

Figure 9A:
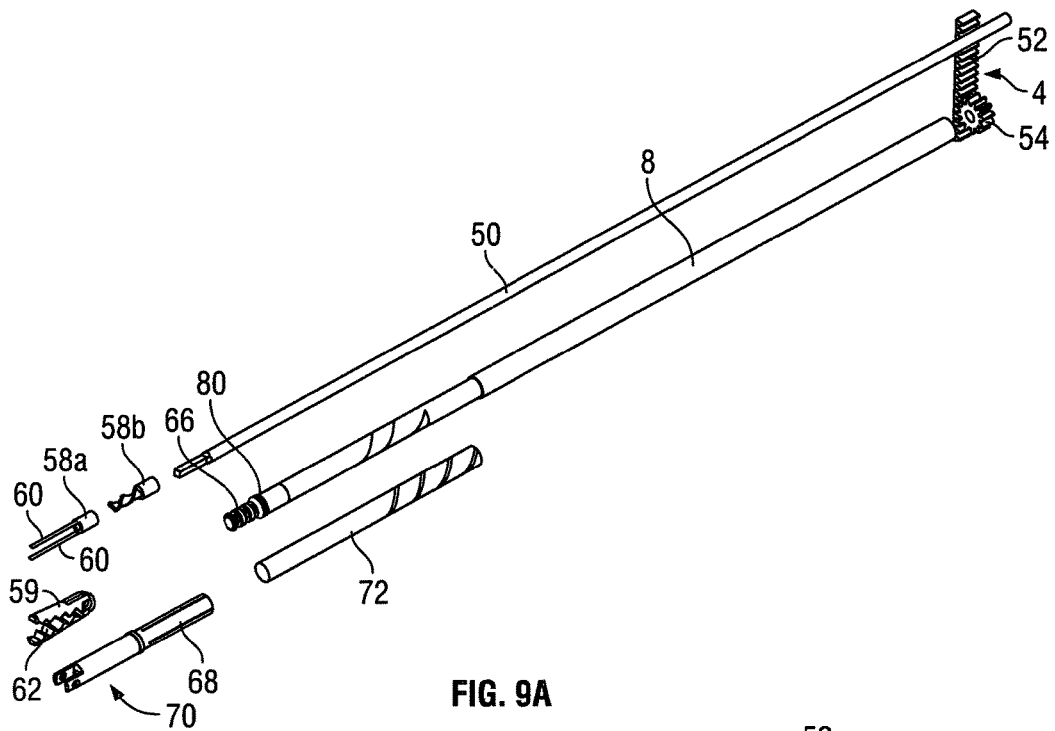
FIG. 9 is a schematic representation of a component linking the user operable input arrangement to the tool head.
Figure 9B:
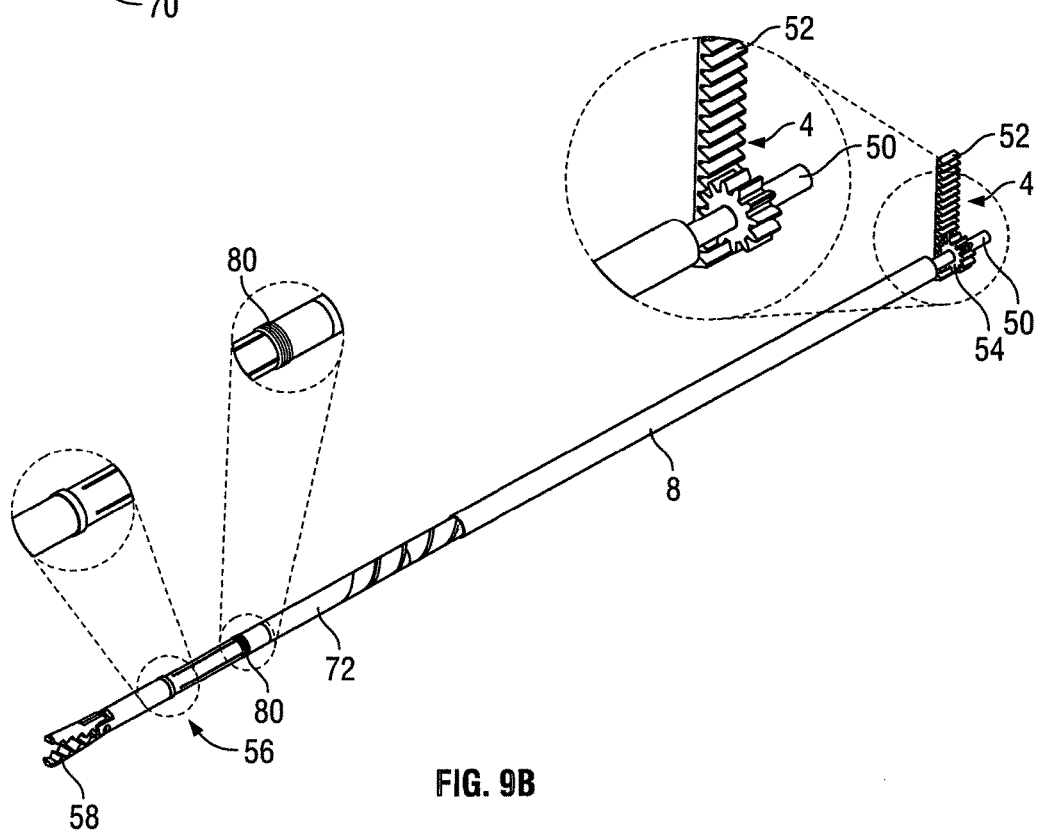

Referring now to FIGS. 9a and b, the manner in which the tool (9) is controlled and also received by the probe (8) will be more carefully described. FIG. 9a shows the component parts and FIG. 9b shows these component parts assembled ready for use via actuation of the trigger (14).

Referring to FIG. 5a, there is a probe (8) which is arranged to receive the drive element (5). As such the drive element (5) passes through the probe (8).

The user operable input arrangement (4) has been represented in schematic form to show a rack and pinion type arrangement whereby depressing the trigger (14) causes movement of component (52) causing linear movement thereof whilst also effective rotation of the cog (54). The cog (54) is secured to the drive element (50) as represented in FIG. 9b thereby effecting rotation of the drive element (50). The cog (54) is accordingly adhered to the drive element (50). The distal end of the drive element (50) is shaped to have a cross-sectional profile to be received in a socket within the tool head (56). The tool head is beneficially made up of a tool element (58) which in the exemplary embodiment is a grasper but that may alternatively comprise, for example, a cutter, finger, scissor etc. The tool head also includes a tool actuator including a tool element contact portion (58a) and a driver (58b) where the driver includes a socket correspondingly shaped to receive the distal end of the drive element (50). As such rotation of the drive element (50) also causes rotation of the driver (58b). The driver (58b) has a portion having an external profile utilising an Archimedes screw principle and is received in the tool element contact portion which has a similar internal configuration to receive the Archimedes screw. As the tool element contact portion (58a) is retained to prevent rotational movement, rotation of the drive element (5) and driver (58b) causes associated axial movement of the tool element contact portion (58a). The tool element contact portion (58a) includes a plurality of fingers (16) configured to seat onto the jaws (62) of the tool head. In one embodiment the jaws (62) are spring loaded to a closed configuration and the fingers (60) seat into corresponding recesses provided in the outer surface of each of the jaws (62). In use therefore as the trigger (14) is depressed, the drive element (50) and driver (58b) are rotated causing axial movement away from the tool element forcing open the jaws (62) against the action of the spring element. In this manner safe control of the opening of the jaws (62) is achieved.

Referring now to the probe (8), this probe (8) projects from the user operable input arrangement (4). At a distal end thereof there is an engaging portion (66) preferably comprising a male engaging portion (66) which is adapted to be received in a female engaging portion (68) provided in the tool body (70) of the tool head. The female engaging portion (68) beneficially is provided by a plurality of fingers defining an opening enabling radial expansion of the fingers as the axially profiled outer surface of the male engaging portion (66) seats into the female engaging portion (68). The opposing end of the tool body (70) is adapted to be secured to the tool element (59).

Figure 10A:
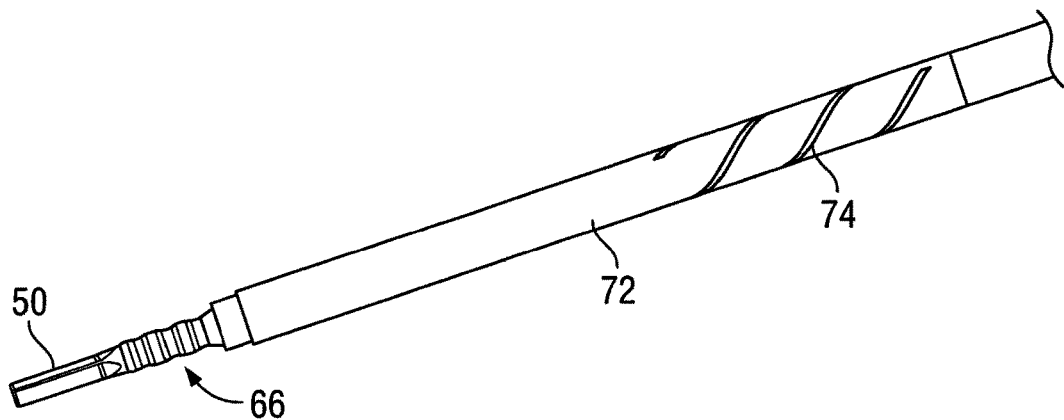
FIG. 10a is a schematic representation of the elongate housing and distal end of the drive element in a primed configuration for communication with a tool head, according to aspects of the present invention.
Figure 10B:
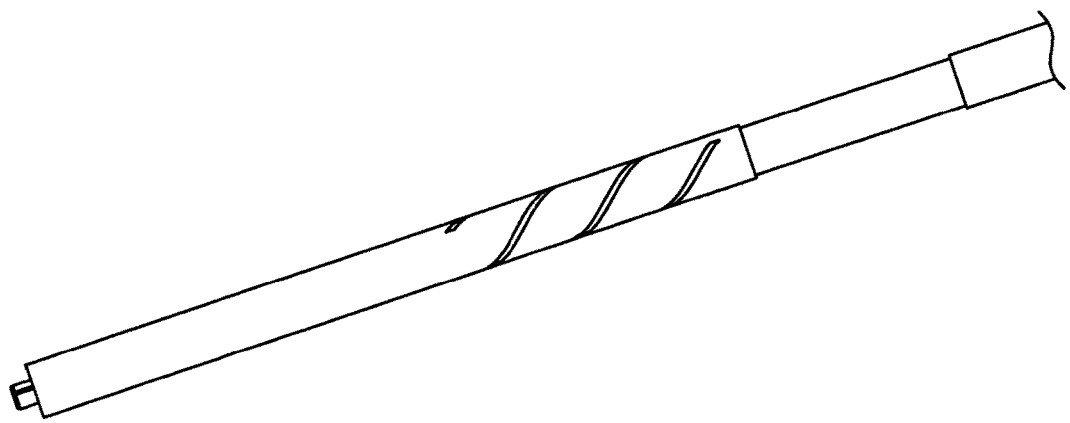
FIG. 10b shows the locked configuration whereby a tool head (not shown) is secured to a drive element and elongate housing according to aspects of the present invention.

As shown more clearly in FIGS. 6a and 6b, in FIG. 10a an actuator (34) is depressed on the magazine (2) which causes axial withdrawal of a collar (72). This exposes the male engaging portion (66). FIG. 10a also shows the driver element (50) projecting out of the end of the male engaging portion (66). As the collar (72) has been retracted along helix (74) the male engaging portion (66) can be inserted into the female engaging portion (68). During this time the actuator (34) must remain depressed. Upon release of the actuator (34) the collar (72) rotates along helix (74) projecting over the fingers of the female engaging portion (68) thus ensuring the engagement between the elongate housing (8) and the tool head. This action occurs within the confines of the magazine to enable engagement and release of the elongate housing and the tool head.

The probe (8) also comprises a screw thread (80) thereon provided to prevent accidental release of the collar (72) whilst also enabling the collar (72) to be secured off the probe (8) for cleaning.

In use the user operable input arrangement including the elongate housing extending therefrom is inserted into the outwardly tapered inlet (16) defining the opening to the extension (30). A control arrangement (not shown) may ensure that there is correct alignment of the magazine with the extension (30) to ensure that the correct medical intervention is to be utilised. This may be programmable and computer controlled. This may alternatively or in addition be selectable via the operator. The operator may select and confirm the tool and a gate is optionally provided which is opened provided in the positioning arrangement to enable the elongate housing and in particular the male engaging portion (66) at the distal end thereof to pass through the seal of the selected chamber. The actuator (34) then is depressed to withdraw the collar allowing engagement between the male engaging portion (66) and the female engaging portion (68). The actuator (34) is then released causing the collar to rotate back to the locked configuration preventing release of the tool (56) from the probe (8). It will be appreciated that described herewith is a tool such a grasper where it will be appreciated by the skilled addressee that the magazine may accommodate drugs for example for transfer to the point of procedure.

Once locked a second gate may be provided in the positioning arrangement which may be opened following secure engagement. In any event, the tool (56) is passed through the outlet access port and through the seal and transferred down the cannula (6) to the distal end thereof at the point of procedure (10). The surgeon can then carry out the procedure as appropriate. Following completion the user operable input arrangement (4) is withdrawn by the operator until the tool (56) reaches the magazine (2). Complete withdrawal is prevented and release of the tool (56) may only be achieved by depression of the actuator (34) which has the effect of axial movement of the collar (72) enabling release of the male and female engaging portions (66 and 68). The magazine can then be rotated to the appropriate subsequent tool and the procedure repeated. A module (32) including the used tool may be extracted from the magazine for cleaning or alternatively the tool may be retained in the magazine until the procedure is completed and all tools are cleaned at once.

Aspects of the present invention have been described by way of example only and it will be appreciated by the skilled addressee that variations and modifications may be made without departing from the scope of protection afforded by the appended claims.

The invention claimed is:

1. A magazine for a surgical apparatus, comprising:
   a plurality of modules configured to be removable from the magazine, each module including a chamber therein,
   each chamber extending between an inlet access port and an outlet access port of each chamber, each chamber adapted to store a medical instrument, and the inlet access port and the outlet access port adapted for passage of the medical instrument.

2. A magazine according to claim 1, wherein each module is laterally removable from the magazine.

3. A magazine according to claim 1, wherein the magazine defines a plurality of slots for receipt of the modules.

4. A magazine according to claim 3, wherein each of the slots and modules are adapted to mate in only one orientation.

5. A magazine according to claim 1, wherein the modules each include an identifier for identifying the medical instrument therein.

6. A magazine according to claim 1, wherein the modules are disposed around a longitudinal axis.

7. A magazine according to claim 1, further comprising a plurality of medical instruments in the plurality of chambers.

8. A magazine according, to claim 1, wherein the inlet access port and the outlet access port of each of the chambers are aligned in a longitudinal axis.

9. A magazine according to claim 1, wherein the inlet access port and the outlet access port of each of the plurality of chambers are sealed.

10. A surgical apparatus comprising a magazine according to claim 1, the apparatus further comprising:
   a probe adapted to interchangeably mate with the plurality of medical instruments wherein the inlet access port enables the probe to extend into the chamber and mate with the medical instrument therein and the outlet access port enables passage of the probe including the medical instrument therefrom;
   a first guide portion for guiding the probe to the magazine;
   a second guide portion aligned with the first guide portion for guiding the probe from the magazine; and
   a positioning arrangement arranged to enable movement of the magazine relative to the first and second guide portions to enable selective alignment of the first and second guide portions with one of the plurality of chambers to enable passage of the probe therethrough.

11. An apparatus according to claim 10, wherein the positioning arrangement includes a frame adapted to enable the magazine to rotate relative to the first and second guide portions.

12. An apparatus according to claim 11, wherein the frame has first and second magazine engagement elements spaced apart in a longitudinal axis.

13. An apparatus according to claim 10, further comprising a motor for causing movement of the magazine relative to the first and second guide portions.

14. An apparatus according to claim 10, wherein the second guide portion comprises a proximal end in communication with the outlet access port of a chamber and a distal end having an opening for enabling a medical instrument to pass therethrough, the second guide portion including at least one access port, wherein the at least one access port is closer to the proximal end of the second guide portion than the distal end of the second guide portion.

* * * * *